United States Patent [19]

Malang

[11] 4,245,500
[45] Jan. 20, 1981

[54] SENSOR FOR DETERMINING HEAT FLUX THROUGH A SOLID MEDIUM

[75] Inventor: Siegfried Malang, Linkenheim, Fed. Rep. of Germany

[73] Assignee: Kernforschungszentrum Karlsruhe GmbH, Karlsruhe, Fed. Rep. of Germany

[21] Appl. No.: 974,498

[22] Filed: Dec. 29, 1978

[30] Foreign Application Priority Data

Dec. 30, 1977 [DE] Fed. Rep. of Germany ....... 2758994

[51] Int. Cl.³ ............................................. G01K 17/00
[52] U.S. Cl. .............................. 73/190 H; 73/DIG. 7
[58] Field of Search .................. 73/15 R, 190 H, 241, 73/DIG. 7

[56] References Cited

U.S. PATENT DOCUMENTS

| | | | |
|---|---|---|---|
| 3,233,458 | 2/1966 | Vrolyk | 73/190 |
| 3,267,726 | 8/1966 | Sellers | 73/190 |
| 3,526,123 | 9/1970 | Putman | 73/15 |
| 3,724,267 | 4/1973 | Zoschak | 73/190 |

Primary Examiner—Herbert Goldstein
Attorney, Agent, or Firm—Spencer & Kaye

[57] ABSTRACT

A measuring sensor for use in determination of the heat flux through a solid medium according to the method in which two thermoelements are arranged at a defined distance and a temperature gradient of the medium is measured from which the heat flux is determined, composed of a body shaped to be fitted into an opening provided in the medium to be axially penetrated by the heat flux through the medium while the lateral surface of the body is thermally insulated from the medium, and constructed such that the integrated coefficient of thermal conductivity of the body is substantially equal to the coefficient of thermal conductivity of a volume of the medium having dimensions corresponding to those of the opening, the body including components of two different thermoelectric materials defining at least two spaced thermoelectrically effective contact points, and signal leads associated with the contact points and spaced apart in the direction of the heat flux; and wherein the exterior lateral surface of said body is insulated from the medium.

9 Claims, 3 Drawing Figures

SENSOR FOR DETERMINING HEAT FLUX THROUGH A SOLID MEDIUM

BACKGROUND OF THE INVENTION

The present invention relates to a measuring sensor for determining heat flux through a solid medium, such as, for example, the cooled walls of a heating rod, the measurement being effected by arranging two thermoelements at a defined distance to effect a measurement of a temperature gradient of the mwedium, from which the heat flux is determined.

In many cases, heat flux in the interior or on the surface of bodies must be determined experimentally. Aside from the very integral method of determining a heat balance, there exist basically two different methods: measurement of the temperature gradient; and measurement of the temperature at one point, and determination of the heat flux by solving the so-called inverse heat conduction problem.

If, for example, the heat flux which is transmitted from the wall of a tube to a medium flowing through the interior of the tube is to be measured by measurement of the temperature gradient, two separate thermoelements are usually installed in the wall of the tube at different distances from its interior surface. The heat flux is calculated from the difference between the two temperatures, the distance between the points of mesuretment and the heat conductivity of the tube wall. In many cases, however, this method fails because the dimensions are too small and the attainable accuracy is insufficient.

If, for example, a heat flux of 5 $W/cm^2$ is to be determined by means of two thermoelements disposed at a distance of one millimeter, the temperature to be measured in a stainless steel wall is about 2.5° K. If at a temperature of 500° C. each one of the two temperatures is determined with an accuracy of ±1 per thousand, this tolerance alone results in an inaccuracy in the heat flux of ±40%. An additional inaccuracy is produced in the determination of the distance between the measuring locations, which without damage can be determined only roughly, and, even when a transverse cut is made in the tube wall, can be effected with an accuracy of ±0.05 mm, at most. Added to this is the interfering effect which the thermoelements have on the heat flow. For these reasons, this method can be used with sufficient accuracy only with large heat fluxes and relatively thick-walled tubes.

The method based on measurement of the temperature at one point and determination of the heat flux by solution of the inverse heat conduction problem can be used only for one-dimensional problems.

If, for example, the transient heat flux at the surface of a rod is to be measured, a thermoelement is usually installed in the outer layer of the rod and is used to measure the temperature directly below the surface of the rod as a function of time. The resulting temperature profile in the rod is calculated, taking into consideration the rod structure, including possible contact resistance between various layers The heat flux is then varied in steps over a period of time to permit determination of that heat flux for which the temperature calculated for the site of the thermoelement coincides with the measured temperature. The solution of this inverse heat conduction problem often produces numerical instabilities which can be avoided only at considerable expense and which adversely influence the accuracy of the measurement.

However, the most significant adverse influence on the accuracy of this method is a lack of knowledge of the thermal behavior of the rod. Particularly the contact resistances pose a great uncertainty.

SUMMARY OF THE INVENTION

It is thus an object of the present invention to provide a measuring sensor which is as small as possible and which can be installed in a wall, interferes as little as possible with the flow of heat in the wall, and furnishes an electrical voltage which is proportional to the temperature drop over a defined layer thickness.

A further object of the invention is to provide a sensor which can be calibrated before it is installed.

Another object of the invention is to provide a sensor which is usable for measuring the transient heat flux at the surface of balloon-shaped thicker portions in electrically heated fuel rod simulators.

These and other objects are achieved, according to the invention, by the provision of a measuring sensor for use in determination of the heat flux through a solid medium according to the method in which two thermoelements are arranged at a defined distance and a temperature gradient of the medium is measured from which the heat flux is determined, which sensor is composed of a body shaped to be fitted into an opening provided in the medium to be penetrated by the heat flux through the medium and constructed such that the integrated coefficient of thermal conductivity of the body is approximately equal to the coefficient of thermal conductivity of a volume of the medium corresponding to the opening, the body including components of two different thermoelectric materials defining at least two spaced thermoelectrically effective contact points, and signal leads associated with the contact points and spaced apart in the direction of the heat flux, and wherein the exterior lateral surface of the body is insulated from the medium.

In accordance with preferred embodiments of the invention, a layer of material is disposed between the thermoelectric points of contact, which layer of material influences the temperature gradient in the sensor body and constitutes the one material component that both thermoelectric points have in common.

According to a further advantageous embodiment of the invention, a layer of the other material component of each point of contact is applied to both sides—when seen in the direction of the flow of heat—of the material layer serving as the common material component by means of explosion welding, friction welding or the like.

According to a particularly advantageous embodiment of the invention, the body of the sensor has a circularly cylindrical shape, is composed of a plurality of superposed layers of the thermoelectric materials and a longitudinally cylindrical bore is provided in the interior of the body in which the leads to the sensor are connected to the two outer layers. It is here of particular advantage that the leads are provided by a multiconductor, sheathed thermoelement which is introduced into the bore from the side of through an end face thereof, the conductors of the thermoelement being made of the same materials as the layers of the sensor body. Two conductors of the thermoelement advantageously are made of the same material as the two outer thermoelectric layers or components in the sensor body and are connected thereto.

In order to form a further measuring point in the sensor, with which the temperature inside the sensor can be determined additionally, the thermoelement can be provided with a further conductor made of a different thermoelectric material, preferably of the same material as the center layer, and which is thermoelectrically connected to one of the two other thermoelectric components or layers, respectively, to form a further thermoelectric point, or junction.

A particular advantage of the present invention is the fact that the sensor can be calibrated. To this end, there is provided, according to the invention, a calibrating device which includes a vacuum vessel in which a heating element is disposed and into which the sensor can be inserted with its leads protruding from the vessel. In the calibrating device according to the invention, the heating element is in the form of a rod on one end face of which the sensor can be placed, the sensor and heating rod are surrounded by an additional radiation shield in the interior of the vacuum vessel, and a second rod is provided for dissipating heat from the interior of the vessel to the outside, the second rod being in communication with the sensor at the end of the sensor facing away from the heating rod or its upper layer, respectively.

The formation of two thermocouples with metallic connections of several layers makes it possible to tap potential differences between two layers and obtain from them a direct indication of the quantity of heat flowing integrally through the sensor. The space requirement of the sensor and its installation costs are much less than in the prior art methods. Since the temperature drop is measured directly and no longer need be determined from the difference of two measured temperatures, the accuracy is much greater particularly for smaller heat fluxes. Moreover, the sensor according to the invention, can be calibrated very easily and accurately.

DESCRIPTION OF THE PREFERRED EMBODIMENTS

Figure 1:
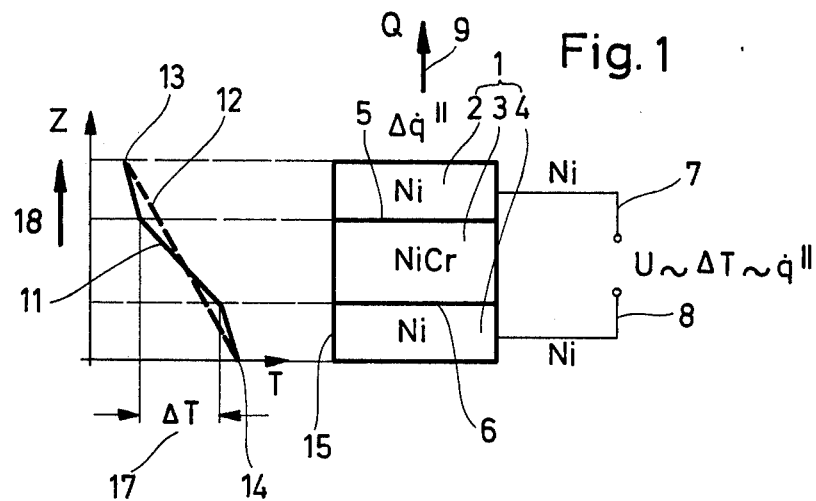
FIG. 1 is a pictorial view illustrating the principle of the sensor according to the invention.

In FIG. 1 which shows the principle of a measuring sensor according to the invention, the body 1 of the sensor is preferably of circularly cylindrical shape and is built up from three superposed layers 2, 3 and 4. For a sensor to be used for a range up to about 1000°, the center layer 3 is made of a nickel-chromium alloy of known composition and the two outer layers 2 and 4 are of pure nickel. Such a sensor is intended for measurements of the heat flux in fuel element sleeves for fast breeder reactors made of chromium-nickel steels. The three layers 2, 3 and 4 of the sensor are connected together by explosion welding so that two thermoelectrically effective points or contact layers 5 and 6 are produced at the points of connection of the outer layers 2 and 4 with the center layer 3. The connection of the individual layers can also be effected by vapor-deposition or by friction welding.

Figure 3:
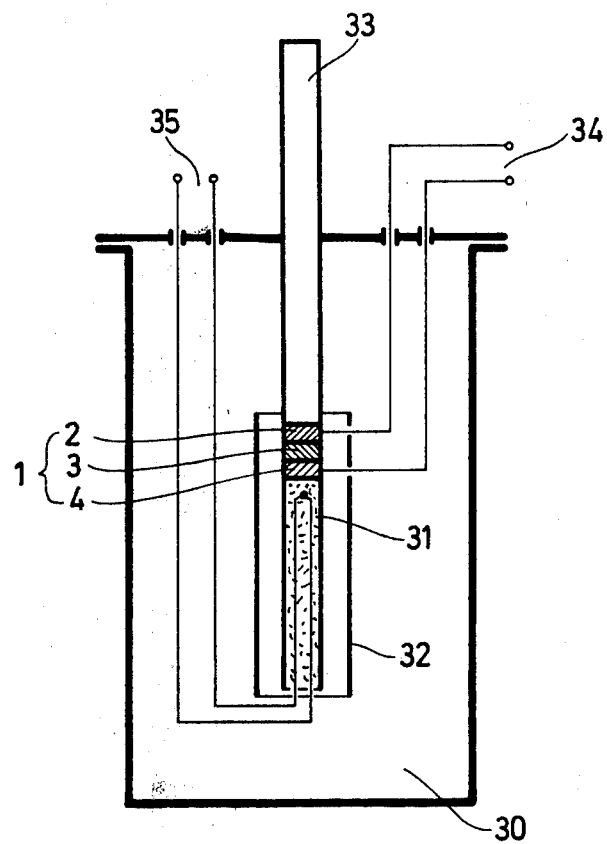
FIG. 3 is a schematic representation of a calibrating device for the sensor according to the invention.

The three layers may be kept very thin and dimensions of approximately 1 mm for the thickness of the entire body 1 are possible. If now the layers 2 and 4 of nickel are connected to nickel wires 7 and 8 a thermally-induced voltage U can be measured between these wires, which voltage is proportional to the temperature differential, $\Delta T$, between layers 5 and 6 from which, with known geometry and coefficient of thermal conduction of the body 1, the heat flux, Q, represented by arrow 9, can be measured by the sensor. The heat flux 9 can be determined either by means of a calibration in a calibrating device according to FIG. 3 or by calculations.

Figure 2:
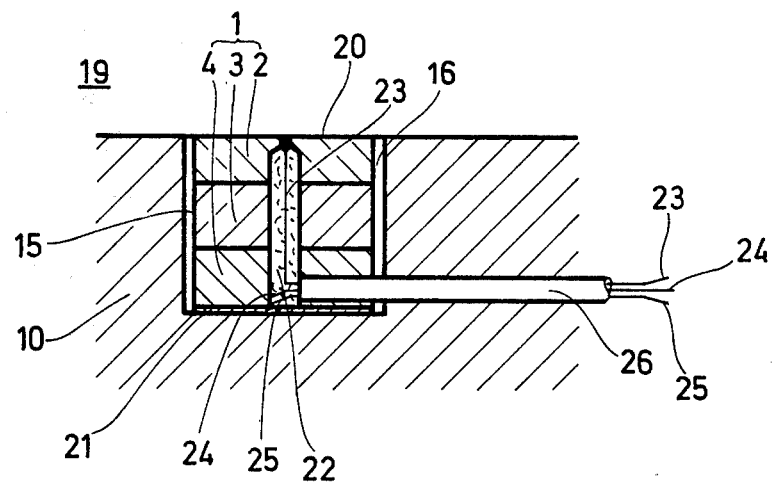
FIG. 2 is a cross-sectional view illustrating an embodiment of a sensor according to the invention installed in a wall or a body.

Definition of the terms Z and $q^{II}$ in FIG. 1:
Space coordinate vertical to the layers: Z[mm]
heat flux: $q^{II}[W/cm^2]$
differential heat flux: $\Delta q^{II}[W/cm^2]$ It is important, however, for the integral coefficient of thermal conductivity of sensor 1 throughout all layers, including its frontal faces to be approximately equal to the coefficient of thermal conductivity which the volume of material removed from the wall 10 for installation of the sensor 1 would have. The integral coefficient of thermal conductivity is the integral, over the entire thickness of body 1, in the direction 9, of the incremental coefficient of thermal conductivity per unit thickness. The temperature gradient in the sensor is shown by line 11, while the temperature gradient which would exist in the same wall region if left intact is shown by line 12. Prerequisite for proper operation of the sensor is that the end points 13 and 14 of the two lines 11 and 12 coincide, and the sensor body 1 is insulated from the wall 10 over its circumference or its lateral wall 15, as shown in FIG. 2. This insulation may be constituted by an air gap 16.

If the sensor body 1 is designed in this manner, it is immaterial what profile the temperature differential $\Delta T$, 17 has in the inner sensor layer 3, it is always the heat flux 9, Q which flows through the sensor in the direction 18 of the temperature decrease.

FIG. 2 shows a schematic representation of an embodiment of the sensor in its installed state. The sensor body 1 is inserted into the wall 10 of a heated rod in a cavity thereof, the cavity preferably being a bore, so that the surface 20 of the sensor body 1 is flush with the surface of the wall 10. The rod is generally arranged to be cooled by a cooling medium 19. The sensor body 1 is composed of a nickel-chromium layer 3 on which, at its two frontal faces, the two nickel layers 2 and 4 are electrodeposited. The lower layer 4 is soldered to the wall 10 at the bottom of the cavity or the bore, respectively, by means of the nickel solder layer 21 so that a good heat connection is produced between sensor and wall. The peripheral surface 15 of the body 1 is insulated from the wall 10 by an annular gap 16.

By suitable selection of the coefficients of thermal conductivity for the three layers 2, 3 and 4, the total coefficient of thermal conductivity of the sensor can be adapted precisely, or as precisely as possible and under consideration of the influence of solder layer 21, the annular gap 15 as well as other irregularities and inhomogeneities of geometry and material of the terminals in the interior of the sensor body 1, to the coefficient of thermal conductivity which the wall 10 would have if it had not been provided with the cavity.

In the sensor embodiment shown in FIG. 2, a hollow longitudinal bore 22 is provided in the sensor 1. A three-conductor jacket thermoelement 26 is brought from the side of the body 1 into its interior 22, the thermoelement having two conductors 23 and 24 of nickel and a further conductor 25 of a nickel-chromium alloy. The two nickel conductors 23 and 24 are connected, in the longitudinal bore 22, to the outer two nickel layers 2 and 4 of the sensor, the nickel-chromium conductor 25 is also connected to one of these two layers, in this embodiment to the layer 4.

The nickel-chromium conductor 25 is connected to the layer 4 and thus forms the thermoelectric junction. The other electric conductor of this junction is formed by the nickel conductor 24 which is also connected to the layer 4 at a distance from the junction of about five times the diameter of the conductors.

Thus it is possible to measure the temperature gradient, ΔT, using conductors 23 and 24 and to effect an additional temperature measurement, using conductors 24 and 25, so that the sensor can also be used to determine the heat transfer coefficient from the tube 10 to the cooling medium 19. The lead-in to the sensor in the form of the thermoelement 26 can be effected toward the side as well as toward the bottom through the frontal faces of the sensor. A lateral groove in the wall 10 which is sealed by soldering, is quite suitable.

As already mentioned, the heat flux through sensor 1 can be calculated from the measured voltage and knowledge of the thickness of the center layer 3, its heat conductivity and the thermovoltages for the pairs of materials employed. It is more accurate, however, to calibrate the sensor by means of the calibrating device which is shown schematically in FIG. 3.

This calibrating device includes a vacuum vessel 30 which is tightly sealed and is provided in its interior with a heating element, or rod, 31 which is surrounded by a radiation shield 32. Within the shield 32, the sensor 1 is placed on rod 31 with its bottom layer 4 in contact with the rod. The upper layer 2 of the sensor is connected with a rod 33 which extends out of the vacuum vessel 30 and which dissipates the heat transferred from the heating rod to the sensor 1 toward the outside. Measuring conductor leads 34 for the sensor 1 and current supply leads 35 for the heating rod 31 are brought out of vessel 30. By changing the heating energy being generated in heating element 31 as well as the rate of cooling of the rod 33 brought out of vessel 30, the heat flux of interest and the temperature range can be examined and the sensor 1 can be calibrated accurately. This calibration is particularly important for the later operation of the sensor and its ability to be calibrated must be considered to be an important advantage of the present invention.

Details of one specific, exemplary operative embodiment of a sensor according to the invention:
Composition of layer 3: Chromel
 90% Ni
 10% Cr
Composition of layer 2,4: Alumel
 24% Ni
 3% Mn
 3% Al
 1% Si
thickness of the layers 2, 3, 4 each = 1[mm]
total Thickness = 3[mm]
diameter of the body 1 = 3[mm]
width of the air gap 16 = 0,1[mm]

It will be understood that the above description of the present invention is susceptible to various modifications, changes and adaptations, and the same are intended to be comprehended within the meaning and range of equivalents of the appended claims.

What is claimed is:

1. A measuring sensor for use in determination of the heat flux through a solid medium according to the method in which two thermoelements are arranged at a defined distance and a temperature gradient of the medium is measured from which the heat flux is determined, said sensor comprising: a body shaped to be fitted into an opening provided in the medium to be penetrated by the heat flux through the medium and composed of materials so selected that the integrated coefficient of thermal conductivity of said body is subtantially equal to the coefficient of thermal conductivity of a volume of said medium having dimensions corresponding to those of said opening, said body including components of two different thermoelectric materials identical to said selected materials of said body and defining at least two spaced thermoelectrically effective contact points; and signal leads associated with said contact points and spaced apart in the direction of the heat flux; and wherein the exterior lateral surface of said body is insulated from the medium.

2. An arrangement as defined in claim 1 wherein said body comprises a layer made of one of said thermoelectric materials which influences the temperature drop in said sensor body disposed between said thermoelectric contact points.

3. An arrangement as defined in claim 2 wherein said layer forms one component of each of said contact points.

4. An arrangement as defined in claim 3 wherein said body further comprises layers of the other one of said thermoelectric materials each plated onto a respective end of said first recited layer by explosion welding, friction welding or the like.

5. Measuring sensor as defined in claims 1, 2, 3 or 4 wherein said body has a circularly cylindrical shape; is composed of a plurality of superposed layers of respective ones of said thermoelectric materials; and is provided at its interior with a longitudinally extending cylindrical bore in which said leads are connected to the two outer layers of said body.

6. An arrangement as defined in claim 5 wherein said leads comprise a multiconductor, sheathed thermoelement which extends into said bore and is composed of a plurality of conductors made of the same materials as said layers.

7. An arrangement as defined in claim 6 wherein two of said conductors of said thermoelement are made of the same materials as the two outermost layers of said body and are connected to said two layers.

8. An arrangement as defined in claim 7 wherein said thermoelement includes a third conductor made of a thermoelectric material different from that of said two layers and thermoelectrically connected to one of said two outermost layers while forming a further thermoelectric point.

9. An arrangement as defined in claim 8 wherein said body is composed of three layers of thermoelectric material and said third conductor is of the same material as the central one of said three layers of said body.

* * * * *